US012569300B2

(12) United States Patent
Soper et al.

(10) Patent No.: US 12,569,300 B2
(45) Date of Patent: Mar. 10, 2026

(54) SYSTEMS AND METHODS RELATED TO ELONGATE DEVICES

(71) Applicant: INTUITIVE SURGICAL OPERATIONS, INC., Sunnyvale, CA (US)

(72) Inventors: Timothy D. Soper, San Jose, CA (US); Troy K. Adebar, Mountain View, CA (US); Christopher R. Carlson, Belmont, CA (US); Vincent Duindam, San Francisco, CA (US); Teresa G. Gadda, Palo Alto, CA (US); Oliver J. Wagner, Mountain View, CA (US); Benjamin G. Cohn, Oakhurst, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 297 days.

(21) Appl. No.: 17/044,354

(22) PCT Filed: Apr. 23, 2019

(86) PCT No.: PCT/US2019/028617
§ 371 (c)(1),
(2) Date: Oct. 1, 2020

(87) PCT Pub. No.: WO2019/209767
PCT Pub. Date: Oct. 31, 2019

(65) Prior Publication Data
US 2021/0100627 A1 Apr. 8, 2021

Related U.S. Application Data

(60) Provisional application No. 62/662,440, filed on Apr. 25, 2018.

(51) Int. Cl.
A61B 34/20 (2016.01)
A61B 1/00 (2006.01)
(Continued)

(52) U.S. Cl.
CPC ................ *A61B 34/20* (2016.02); *A61B 1/00* (2013.01); *A61B 8/12* (2013.01); *A61B 8/4245* (2013.01);
(Continued)

(58) Field of Classification Search
CPC ... A61B 1/00; A61B 10/0233; A61B 17/3403; A61B 18/02; A61B 18/1492;
(Continued)

(56) References Cited

U.S. PATENT DOCUMENTS 5,307,816 A * 5/1994 Hashimoto ........ A61B 17/2258
600/463
5,740,808 A * 4/1998 Panescu ............... A61B 5/6853
600/585
(Continued)

FOREIGN PATENT DOCUMENTS

CN 103619278 A 3/2014
EP 1545365 A1 6/2005
(Continued)

OTHER PUBLICATIONS

International Search Report and Written Opinion for Application No. PCT/US2019/028617, mailed on Aug. 5, 2019, 13 pages.
(Continued)

*Primary Examiner* — Michael J Carey
*Assistant Examiner* — Maria Christina Talty
(74) *Attorney, Agent, or Firm* — Haynes & Boone, LLP.

(57) ABSTRACT

A medical system includes a catheter and a processor. The catheter includes a first channel and a distal end portion associated with a catheter frame of reference. The processor
(Continued)

is configured to receive a first image captured by a first imaging device provided by the catheter within a patient anatomy, and receive a second image of the patient anatomy captured by a second imaging device from outside the patient anatomy. The second image includes the catheter and the first imaging device. The processor is further configured to determine a relative pose between the first imaging device and the distal end of the catheter based on the second image, determine a target location associated with a target structure in the first image, and transform the target location in an image frame of reference associated with the first image to the catheter frame of reference based on the relative pose.

19 Claims, 13 Drawing Sheets

(51) Int. Cl.

| A61B 8/00 | (2006.01) |
| A61B 8/12 | (2006.01) |
| A61B 10/02 | (2006.01) |
| A61B 17/34 | (2006.01) |
| A61B 18/02 | (2006.01) |
| A61B 18/14 | (2006.01) |
| A61B 34/35 | (2016.01) |
| A61M 5/32 | (2006.01) |
| A61M 25/00 | (2006.01) |
| G06T 7/00 | (2017.01) |
| G06T 7/73 | (2017.01) |
| A61B 18/00 | (2006.01) |
| A61B 34/10 | (2016.01) |

(52) U.S. Cl.
CPC ...... *A61B 10/0233* (2013.01); *A61B 17/3403* (2013.01); *A61B 18/02* (2013.01); *A61B 18/1492* (2013.01); *A61M 5/32* (2013.01); *A61M 25/0026* (2013.01); *G06T 7/0014* (2013.01); *G06T 7/74* (2017.01); *A61B 2017/3413* (2013.01); *A61B 2018/00577* (2013.01); *A61B 2034/105* (2016.02); *A61B 2034/2051* (2016.02); *A61B 2034/2061* (2016.02); *A61B 2034/2063* (2016.02); *A61B 34/35* (2016.02); *G06T 2207/10068* (2013.01); *G06T 2207/30021* (2013.01)

(58) Field of Classification Search
CPC .. A61B 2017/00809; A61B 2017/3413; A61B 2018/00577; A61B 2034/105; A61B 2034/2051; A61B 2034/2059; A61B 2034/2061; A61B 2034/2063; A61B 2090/3614; A61B 2090/367; A61B 2090/371; A61B 2090/376; A61B 2090/3784; A61B 34/20; A61B 34/35; A61B 8/12; A61B 8/4245; A61B 90/37; A61M 25/0026; A61M 5/32; G06T 2207/10068; G06T 2207/30021; G06T 7/0014; G06T 7/74
See application file for complete search history.

(56) References Cited

U.S. PATENT DOCUMENTS

| 5,797,849 | A | * | 8/1998 | Vesely | G01S 5/18 |
| | | | | | 600/461 |
| 6,380,732 | B1 | | 4/2002 | Gilboa | |
| 6,389,187 | B1 | | 5/2002 | Greenaway et al. | |
| 6,511,428 | B1 | * | 1/2003 | Azuma | A61N 7/022 |
| | | | | | 601/3 |
| 7,316,681 | B2 | | 1/2008 | Madhani et al. | |
| 9,675,319 | B1 | * | 6/2017 | Razzaque | A61B 6/037 |
| 11,304,686 | B2 | | 4/2022 | Manzke et al. | |
| 2004/0047056 | A1 | | 3/2004 | Sekiguchi et al. | |
| 2005/0180389 | A1 | | 8/2005 | Xenakis et al. | |
| 2008/0283771 | A1 | | 11/2008 | Li | |
| 2008/0286644 | A1 | | 11/2008 | Yeo | |
| 2010/0256558 | A1 | * | 10/2010 | Olson | A61B 34/71 |
| | | | | | 604/95.01 |
| 2011/0319815 | A1 | | 12/2011 | Roelle et al. | |
| 2014/0121502 | A1 | * | 5/2014 | Vignon | A61B 8/0841 |
| | | | | | 600/424 |
| 2014/0142422 | A1 | * | 5/2014 | Manzke | A61B 8/12 |
| | | | | | 600/424 |
| 2014/0187949 | A1 | * | 7/2014 | Zhao | A61B 17/00234 |
| | | | | | 600/443 |
| 2014/0343416 | A1 | | 11/2014 | Panescu et al. | |
| 2015/0305612 | A1 | * | 10/2015 | Hunter | A61B 5/062 |
| | | | | | 600/109 |
| 2018/0064415 | A1 | * | 3/2018 | Zhai | A61N 7/02 |

FOREIGN PATENT DOCUMENTS

| JP | 2009297346 A | 12/2009 |
| JP | 2017515613 A | 6/2017 |
| WO | WO-9836684 A1 | 8/1998 |
| WO | WO-2012158324 A2 | 11/2012 |
| WO | WO-2014106249 A1 | 7/2014 |
| WO | WO-2014186715 A1 | 11/2014 |
| WO | WO-2016191298 A1 | 12/2016 |
| WO | WO-2017139621 A1 | 8/2017 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability and Written Opinion for Application No. PCT/US2019/028617, mailed on Nov. 5, 2020, 9 pages.
Office Action for Chinese Application No. CN201980027428.6, mailed Aug. 26, 2023, 30 pages.
Office Action for Chinese Application No. CN201980027428.6, mailed May 12, 2024. 27 pages.

* cited by examiner

110

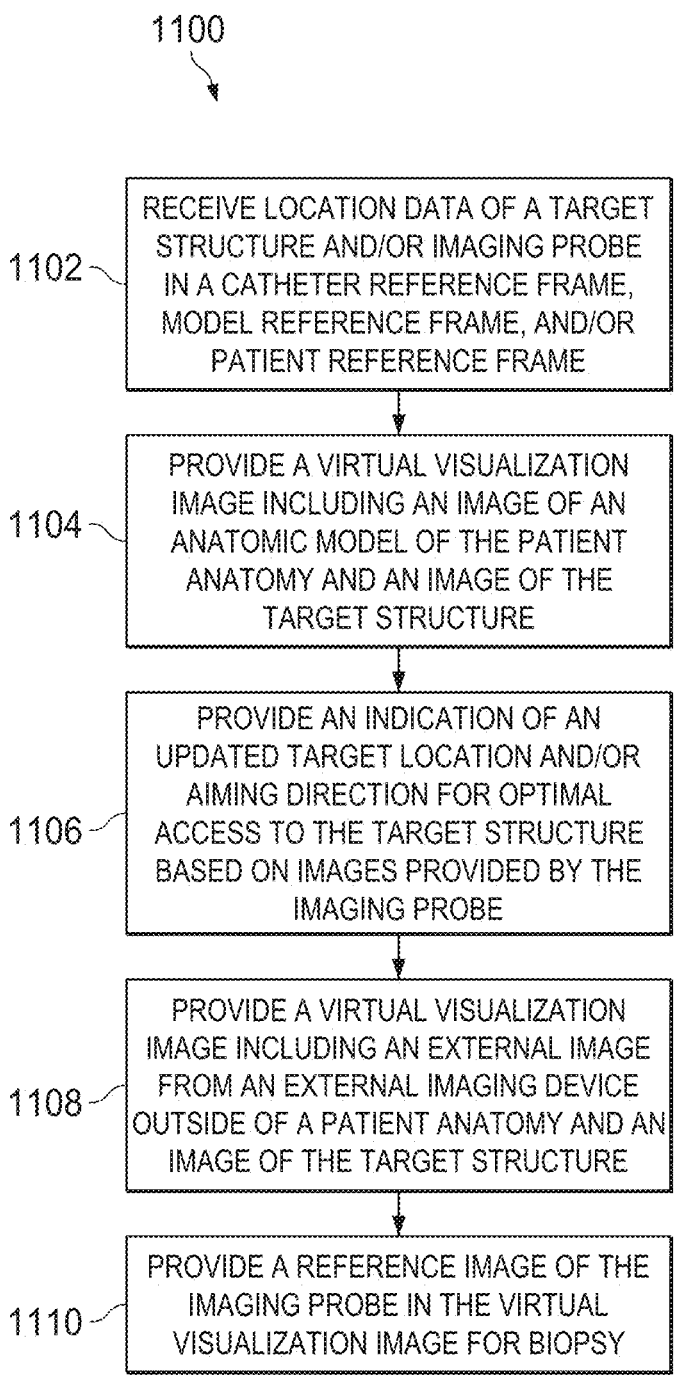

1100

1102 — RECEIVE LOCATION DATA OF A TARGET STRUCTURE AND/OR IMAGING PROBE IN A CATHETER REFERENCE FRAME, MODEL REFERENCE FRAME, AND/OR PATIENT REFERENCE FRAME

1104 — PROVIDE A VIRTUAL VISUALIZATION IMAGE INCLUDING AN IMAGE OF AN ANATOMIC MODEL OF THE PATIENT ANATOMY AND AN IMAGE OF THE TARGET STRUCTURE

1106 — PROVIDE AN INDICATION OF AN UPDATED TARGET LOCATION AND/OR AIMING DIRECTION FOR OPTIMAL ACCESS TO THE TARGET STRUCTURE BASED ON IMAGES PROVIDED BY THE IMAGING PROBE

1108 — PROVIDE A VIRTUAL VISUALIZATION IMAGE INCLUDING AN EXTERNAL IMAGE FROM AN EXTERNAL IMAGING DEVICE OUTSIDE OF A PATIENT ANATOMY AND AN IMAGE OF THE TARGET STRUCTURE

1110 — PROVIDE A REFERENCE IMAGE OF THE IMAGING PROBE IN THE VIRTUAL VISUALIZATION IMAGE FOR BIOPSY

Fig. 11

SYSTEMS AND METHODS RELATED TO ELONGATE DEVICES

CROSS-REFERENCE TO RELATED APPLICATIONS

This application is the U.S. national phase of International Application No. PCT/US2019/028617, filed Apr. 23, 2019, which designated the U.S. and claims priority to and the benefit of U.S. Provisional Application No. 62/662,440, filed Apr. 25, 2018, both of which are incorporated by reference herein in their entirety.

FIELD

The present disclosure is directed to systems and methods for controlling a steerable elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. However, a minimally invasive medical device does not always provide an operator (e.g., a surgeon or other medical personnel) with sufficient imaging capabilities to identify the target tissue location, such as when the target tissue location is located below a surface of a passageway through which the minimally invasive medical device is introduced.

Accordingly, it would be advantageous to provide improved real-time visualization of the target tissue location to aid an operator during minimally invasive medical techniques.

SUMMARY

The embodiments of the invention are best summarized by the claims that follow the description.

Consistent with some embodiments, a method is performed by a computing system. The method includes receiving a first image of an anatomic structure from an imaging probe inside a patient anatomy. The first image has an image frame of reference. The imaging probe is extendable distally beyond a distal end of a catheter. The distal end of the catheter has a catheter frame of reference. The method further includes receiving a first external image of the patient anatomy from a first external imaging device. The first external image includes the catheter and the imaging probe. The method further includes determining a relative pose between the imaging probe and the distal end of the catheter based on the first external image, determining a target location associated with a target structure in the first image, and transforming the target location in the image frame of reference to the catheter frame of reference based on the relative pose.

Consistent with some embodiments, a medical system includes a catheter including a first channel and a distal end portion. The distal end portion is associated with a catheter frame of reference. The medical system further includes a processor. The processor is configured to receive a first image captured by a first imaging device provided by the catheter within a patient anatomy, and receive a second image of the patient anatomy captured by a second imaging device from outside the patient anatomy. The second image includes the catheter and the first imaging device. The processor is further configured to determine a relative pose between the first imaging device and the distal end of the catheter based on the second image, determine a target location associated with a target structure in the first image; and transform the target location in an image frame of reference associated with the first image to the catheter frame of reference based on the relative pose.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 11 illustrates a flowchart describing a method for providing virtual visualization images on a display system according to some embodiments.

Figure 1:
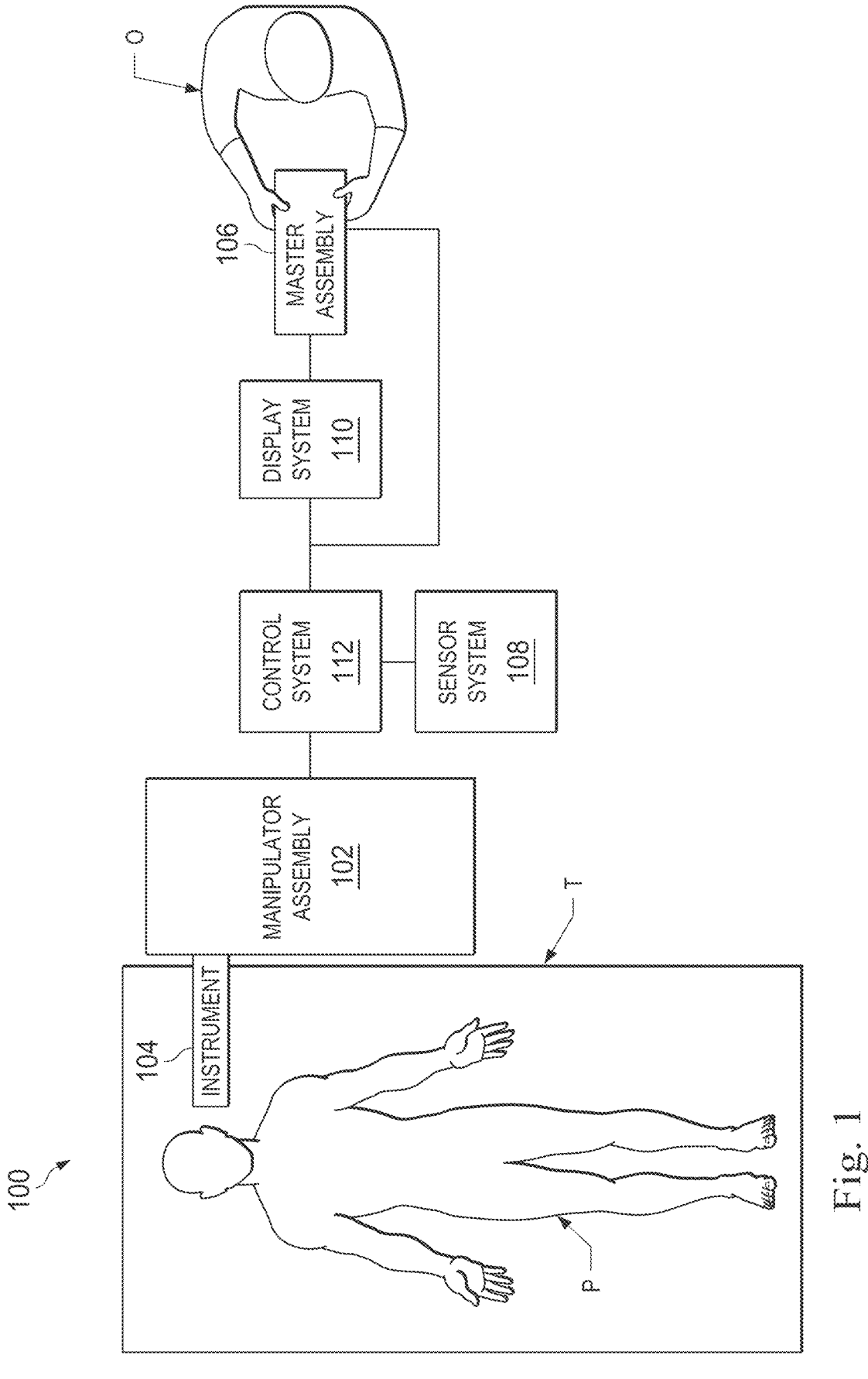
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator (e.g., a surgeon, a clinician, or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth®, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery"), which is incorporated by reference herein in its entirety, discloses such one system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figures 2A, 2B:
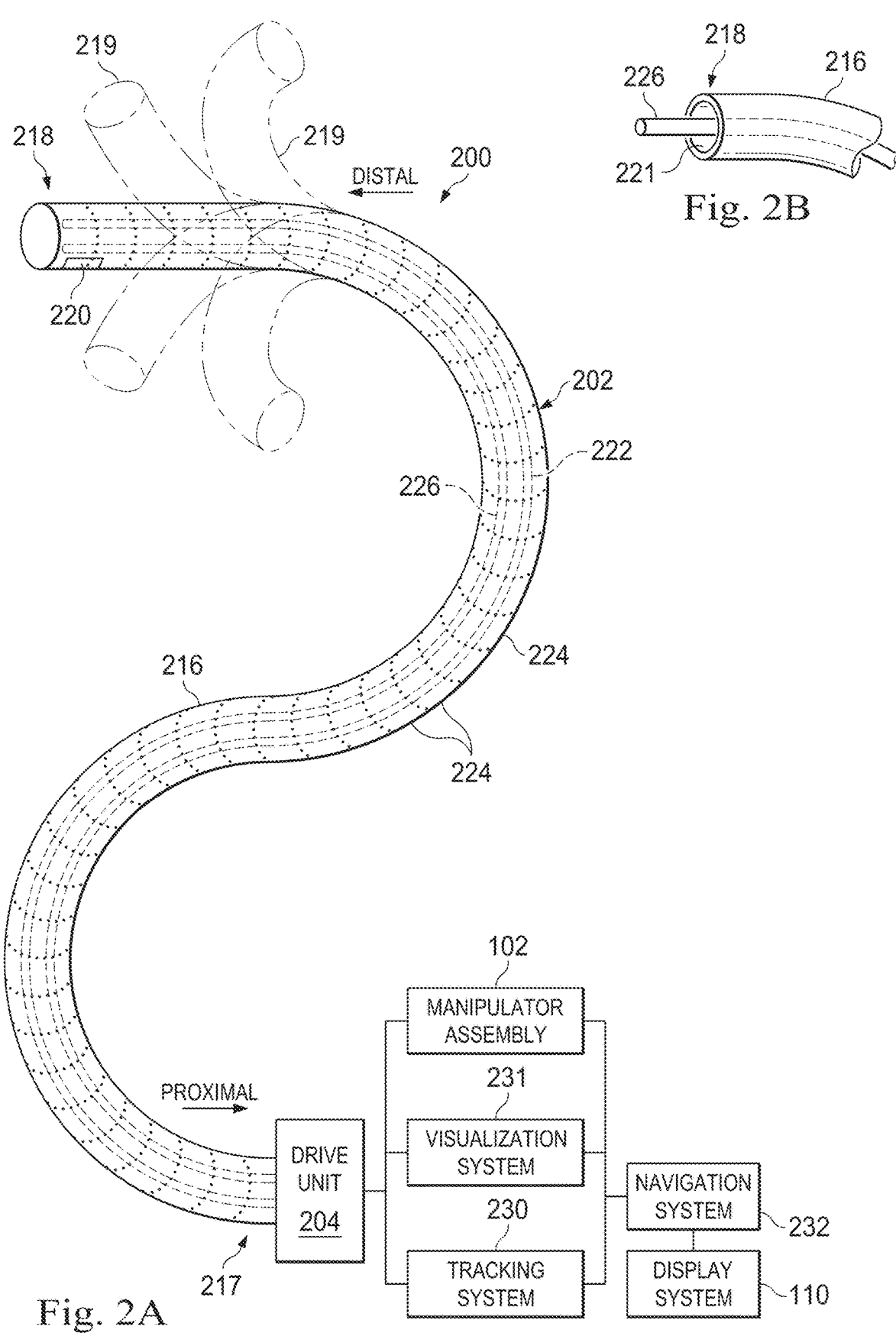
FIG. 2A is a simplified diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably bend the distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models (e.g., anatomic models of the patient anatomy) to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
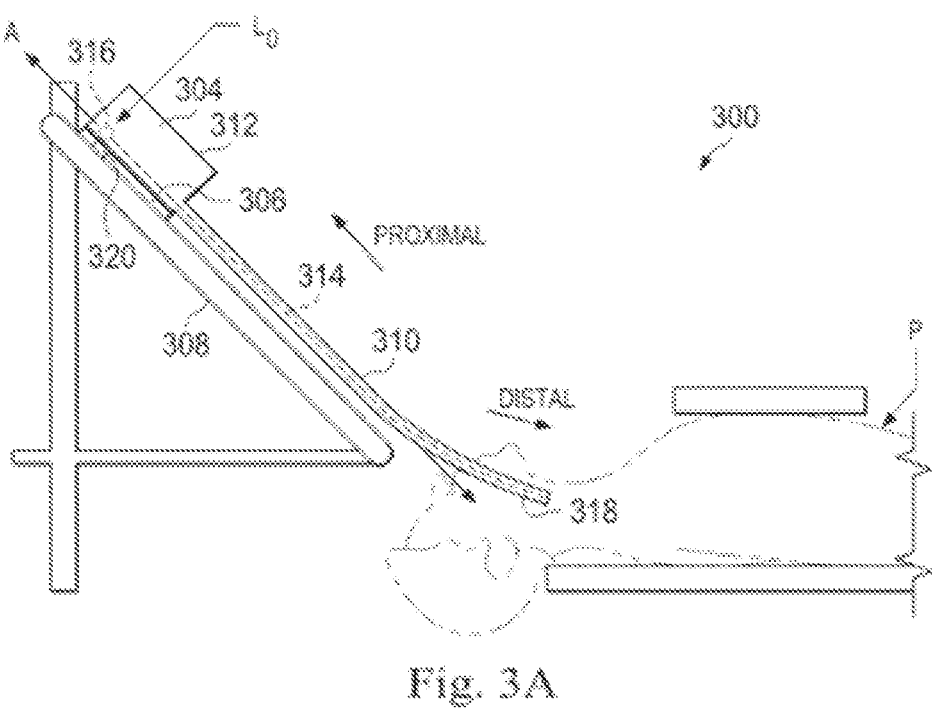
FIGS. 3A and 3B are simplified diagrams of side views of a patient coordinate space including a medical instrument mounted on an insertion assembly according to some embodiments.
Figure 3B:
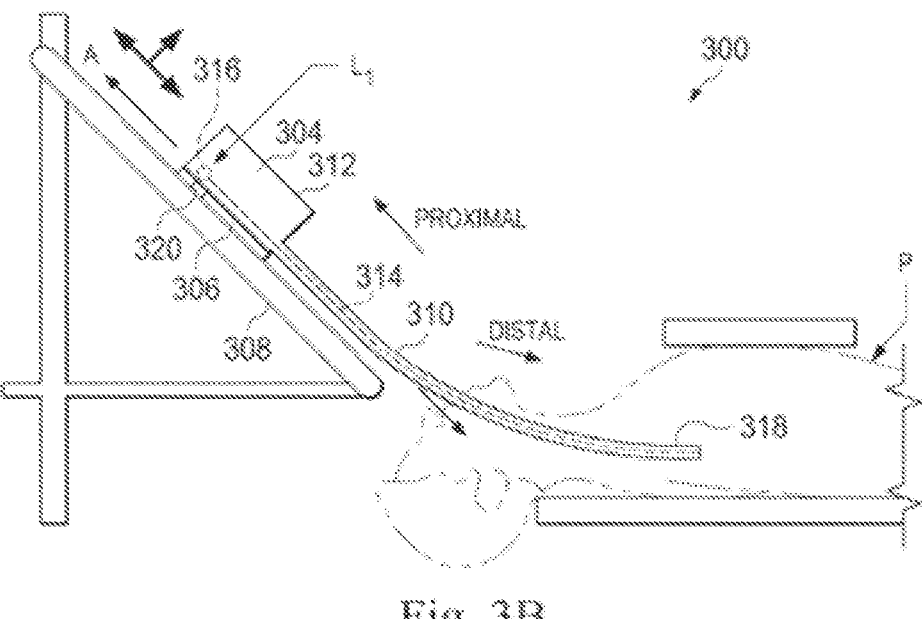

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position Lo on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., 1=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position Lo. In some examples, position $L_1$ may further be used as an indicator of the distance or insertion depth to which distal end 318 of elongate device 310 is inserted into the passageways of the anatomy of patient P.

Figure 4:
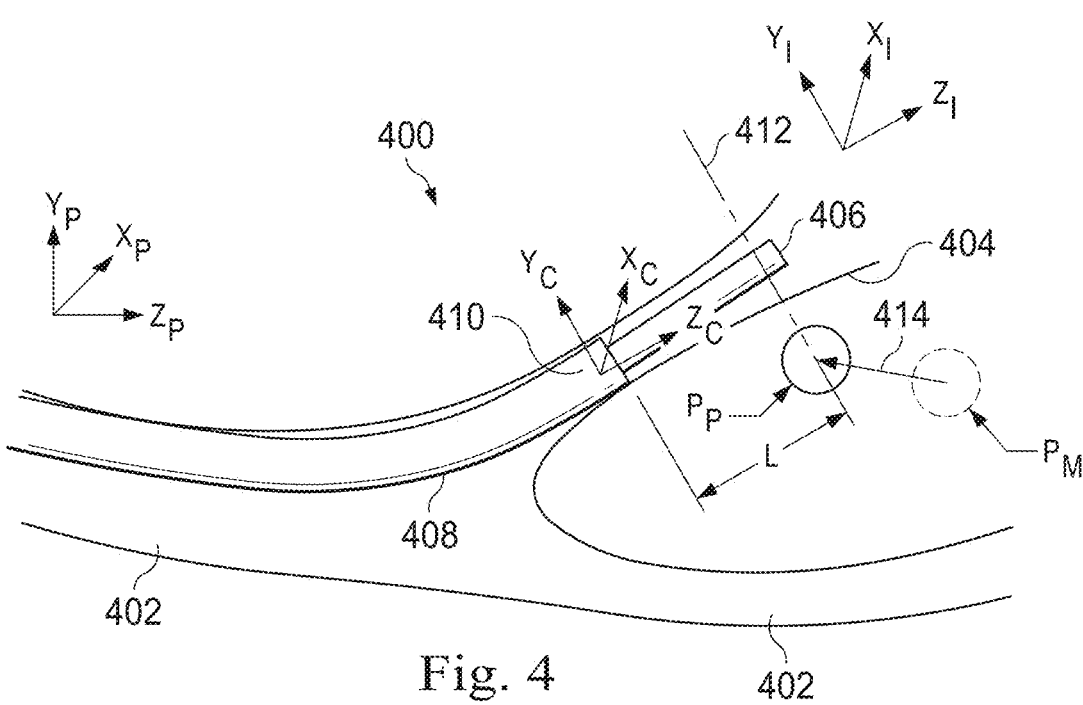
FIG. 4 illustrates a catheter including an imaging system according to some embodiments.
Figure 5:
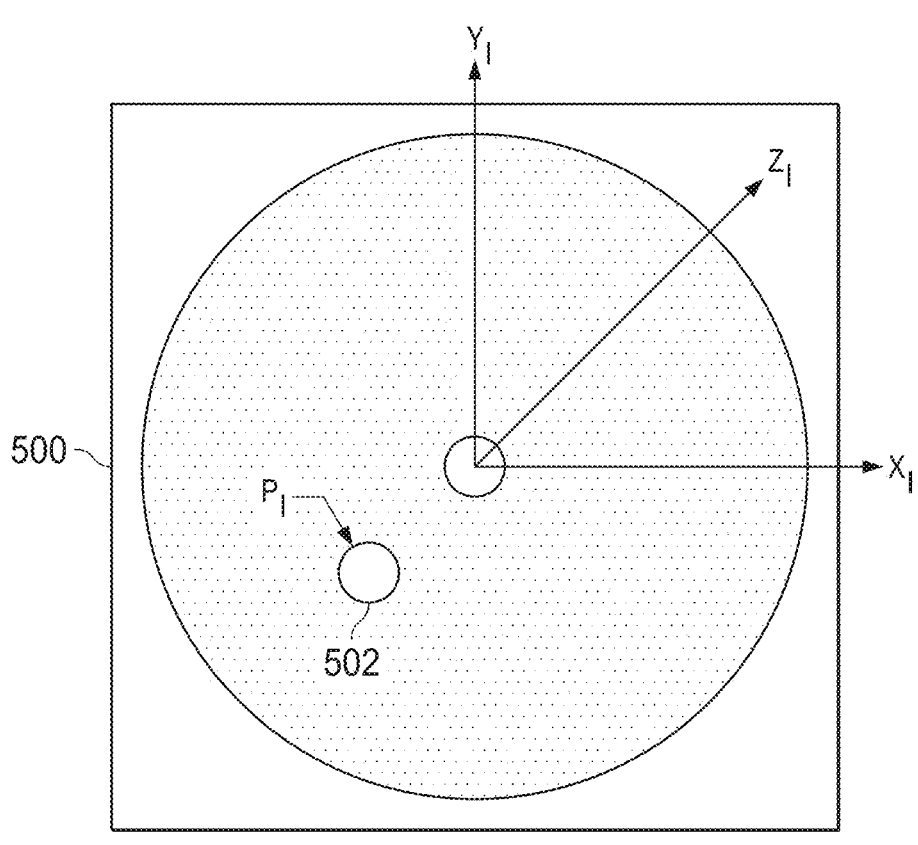
FIG. 5 illustrates an image generated by the imaging system of FIG. 4 according to some embodiments.
Figure 6:
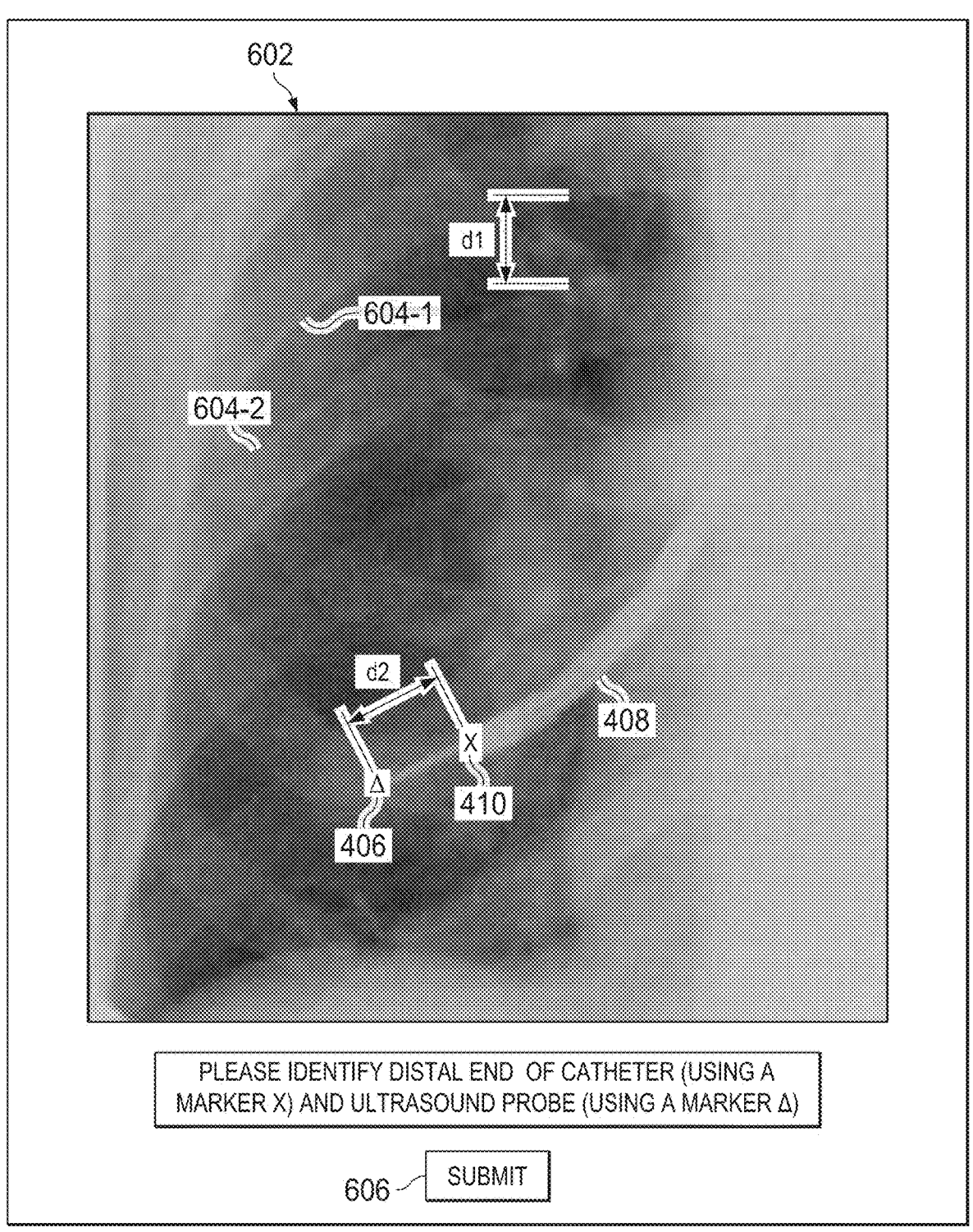
FIG. 6 illustrates an external image of a patient anatomy image generated by an imaging system outside of the patient anatomy according to some embodiments.
Figure 7:
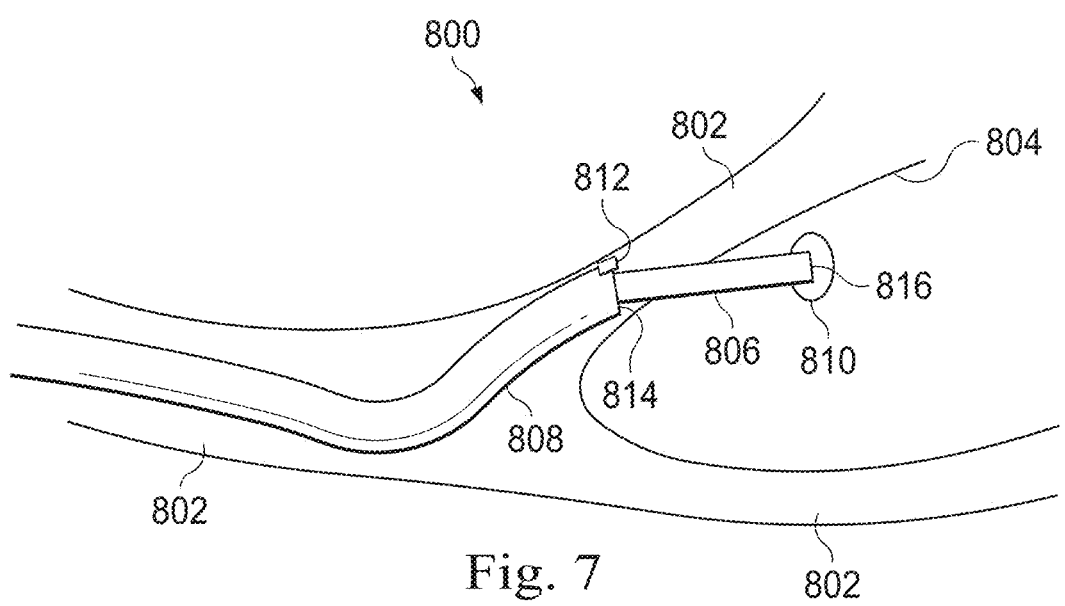
FIG. 7 illustrates a catheter including an imaging system and a tool according to some embodiments.
Figure 8:
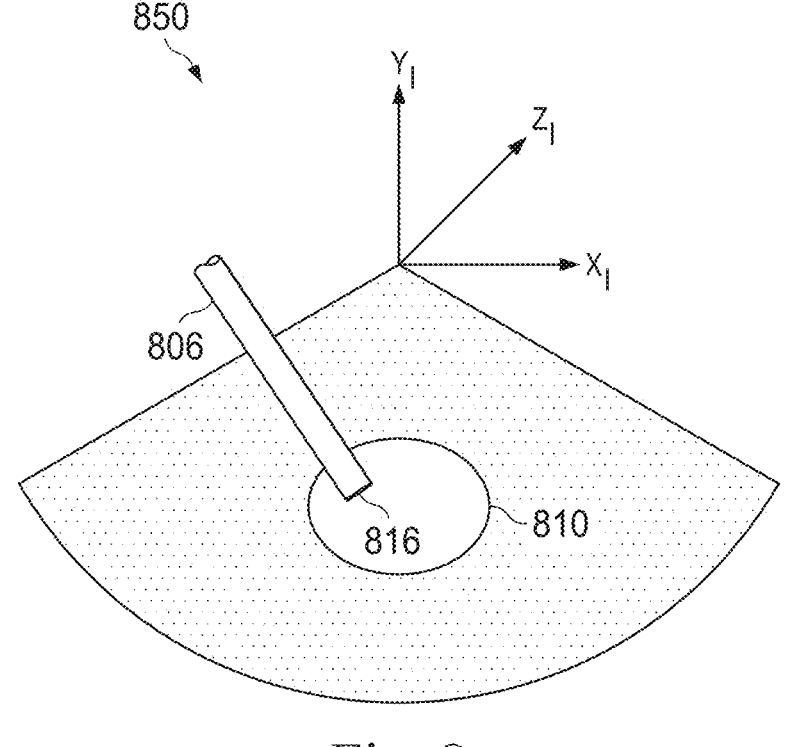
FIG. 8 illustrates an image generated by the imaging system of FIG. 7 according to some embodiments.
Figure 9:
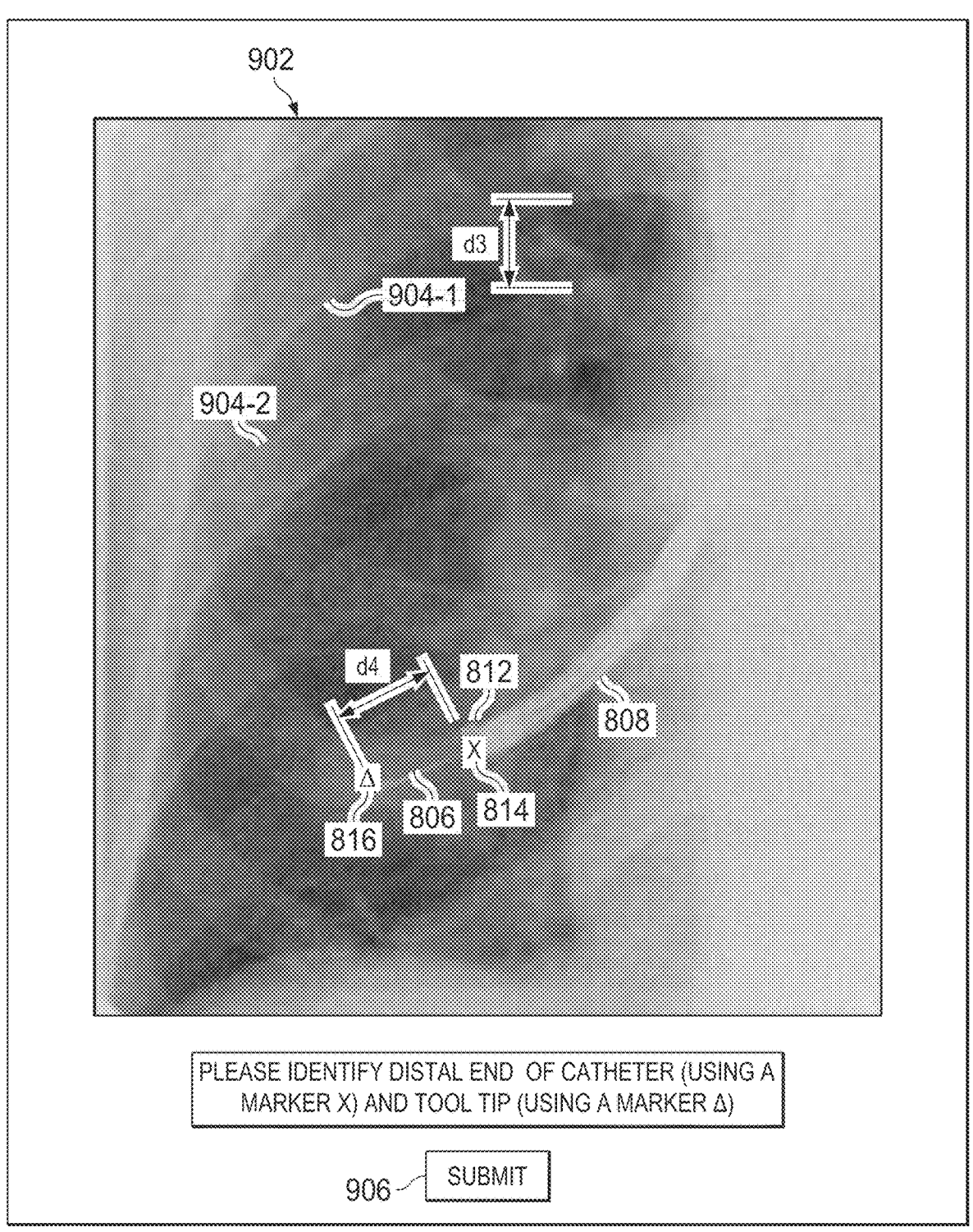
FIG. 9 illustrates an external image of a patient anatomy generated by an imaging system outside of the patient anatomy according to some embodiments.
Figure 10:
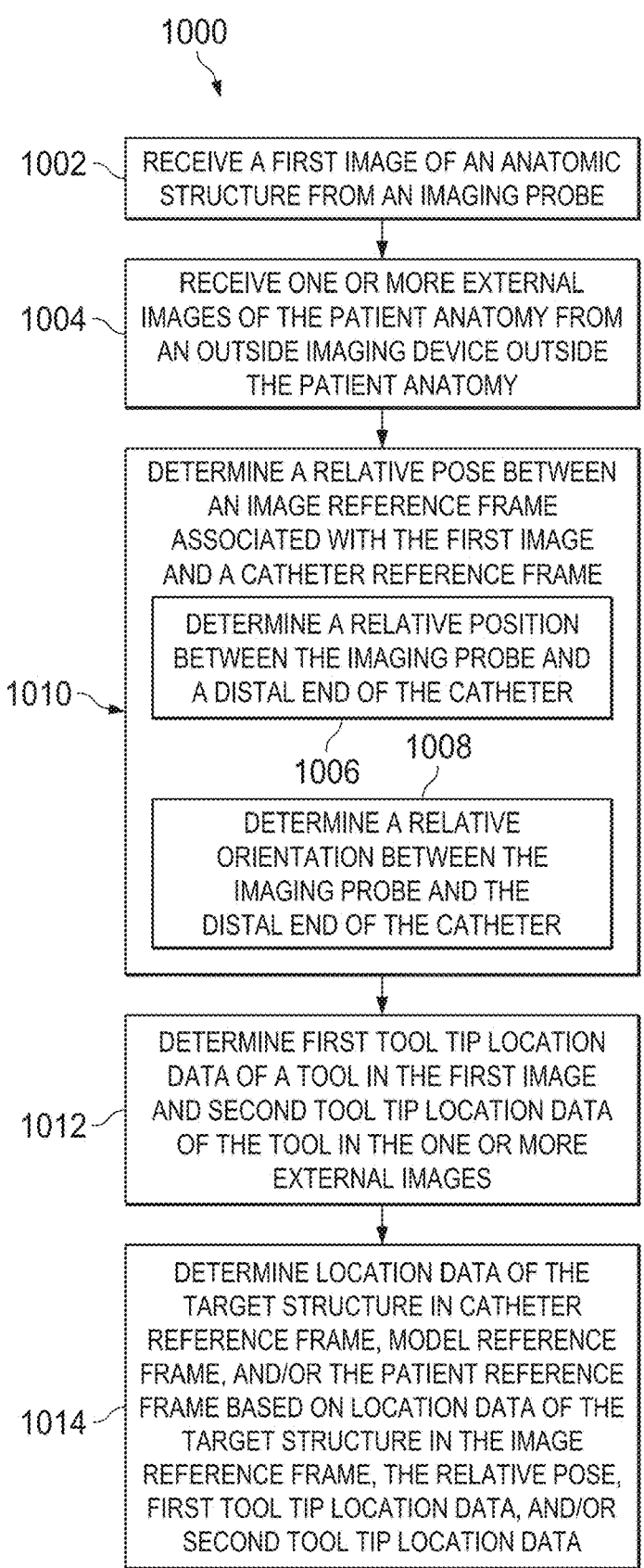
FIG. 10 illustrates a flowchart describing a method for determining a location of a target structure using an imaging system according to some embodiments.

Referring to FIGS. 4, 5, 6, 7, 8, 9, and 10, in some embodiments, the location of the target structure may be confirmed/determined using an imaging probe (e.g., an ultrasound probe) integrated within or delivered by a catheter. In various embodiments, the use of ultrasound technology for determining and/or confirming the target structure location may allow for greater accuracy in biopsy or other focal therapies directed to nodules with small diameters (e.g., approximately 10 mm or smaller). FIGS. 4, 5, and 6 illustrate a catheter including a channel, which may be used for inserting either an imaging probe or a tool. FIGS. 7, 8, and 9 illustrate a catheter configured to provide an imaging probe and a tool concurrently. FIG. 10 illustrates a method for determining a location of a target structure using the imaging probe.

The example of FIG. 4 illustrates a virtual image 400 of a target structure $P_M$ (e.g., a tumor, a lesion, a nodule), and nearby anatomic passageways 402. The passageways 402 include passageway walls 404. The passageways 402 are located in a patient frame of reference with coordinate system (Xp, Yp, Zp). The patient reference frame may be a fixed reference frame (i.e., one that does not move during the medical procedure). The image of the plurality of passageways 402 (e.g. obtained from pre- or intra-operative modeling) may be registered to the patient frame of reference using methods previously described with reference to FIG. 1. The location of the target structure $P_M$ is determined within the pre-operative or intraoperative imaging, and is thus known within the patient frame of reference. In this embodiment, the anatomic passageways are bronchial passageways of the lung, but the systems and methods of this disclosure may be suitable for use in other natural or surgically created passageways in anatomical systems such as the circulatory system, the digestive system, the renal system, and the reproductive system including anatomical structures such as the colon, the intestines, the kidneys, the heart, and/or the like.

The flexible catheter body 408 (substantially similar to flexible body 216) may be navigated to a catheter park location that allows access to a target structure. The catheter may be positioned at the catheter park location in an orientation allowing for a distal end portion of the catheter to be pointed in a direction towards the target structure. In this manner, a tool inserted through the flexible catheter body 408, would be inserted along a pointing vector to the target structure. The catheter may be navigated using, for example, visual endoscopy, EM sensors, and/or optical fiber shape-based navigation techniques. An imaging probe 406 can be inserted through the flexible catheter body 408. In one embodiment, the imaging probe 406 is an ultrasound probe 406. The ultrasound probe 406 may use ultrasound transducers such as side-facing transducers, forward-facing transducers, curved transducers, radial transducers, and/or the like. In an example, the ultrasound probe uses a side-imaging transducer including a rotating ultrasound transducer for imaging in a direction generally perpendicular to the axis of rotation of the transducer. The side-imaging probe generates a cross-sectional (i.e., radial) image along an imaging plane 412. Optionally the ultrasound probe 406 may be integral with the catheter rather than interchangeable as shown in FIG. 4. A catheter frame of reference and coordinate system $(X_c, Y_c, Z_c)$ is defined at the distal end portion 410 of the catheter 408 and is registered with the patient coordinate system using methods previously described with reference to FIG. 1. In the embodiment of FIG. 4, the axis of rotation of the transducer is generally along the Zc direction of the catheter frame of reference.

In some embodiments, a side-imaging probe generates images of the tissue at a radial distance from the axis of rotation, including tissue located outside of the anatomic passageways. In other embodiments, a forward-looking ultrasound probe may be used to image tissue distal of the imaging transducer. The ultrasound probe may be relatively small to navigate narrow anatomical passageways. For example, the ultrasound probe may have distal end diameter of approximately 1.4 mm.

FIG. 5 illustrates an image 500 generated by the ultrasound probe 406 in the imaging plane 412 shown in FIG. 4. The image 500 has an image frame of reference and coordinate system $(X_I, Y_I, Z_I)$. The target structure 502 $(P_I)$ is identified in the image frame of reference. It may be identified, for example, by a clinician, by an image analysis algorithm, or by a combination of the two. The ultrasound scan may be gated for respiratory and/or cardiac cycles. Although the image 500 is two-dimensional, a three-dimensional image may be constructed from a plurality of two-dimensional ultrasound scans. Data associated with the location of the target structure $P_I$ in the image frame of reference is transformed to the catheter coordinate system or the patient coordinate system (that has been registered with the catheter coordinate system) as $P_P$. The location of the target structure $P_P$ as determined by the ultrasound probe may be compared to the location of the target structure $P_M$ determined from pre-operative or intra-operative imaging in the catheter or patient frame of reference to determine a correction vector 414. The correction vector 414 is the offset value between the location of the target structure $P_M$ and the location of the target structure $P_P$.

In various embodiments, to transform the image coordinate system to the catheter coordinate system, the relative three-dimensional pose between the image coordinate system and the catheter coordinate system is determined. In some embodiments, it is measured directly by sensors on the catheter and imaging probe. Such sensors may include an EM sensor, a fiber optic shape sensor, or the like. The sensors on the catheter and the imaging probe do not need to be of the same type.

In some embodiments, the relative pose between the image coordinate system $(X_I, Y_I, Z_I)$ and the catheter coordinate system $(X_C, Y_C, Z_C)$ can be computed by measuring the insertion length L and/or a roll angle of the image coordinate system with respect to the catheter coordinate system, assuming the imaging probe extends straight beyond the tip of the catheter and the pose of the catheter end is known. In some embodiments, the relative pose is determined based on assumptions of the relative position of the target to the catheter distal end (e.g. the catheter end is pointed at the target). In those embodiments, the image probe delivered by the catheter is assumed to lie along the pointing direction of the catheter, and as such, only a distance from the catheter distal end needs to be determined. Such a distance may be an assumed distance, or may be determined using an external imaging. In an example, after determining the target location in the catheter reference frame and the target location in the image reference frame (e.g., from the captured ultrasound image), the transformation between the image reference frame and the catheter reference frame may be determined.

In some examples, the insertion length L may be determined using, for example, an encoder or a stepping motor. The roll angle may be determined using a variety of techniques. For example, an ultrasound probe may include a roll alignment feature keyed to the catheter, where the roll alignment feature causes the ultrasound probe to maintain a fixed orientation about the catheter roll axis (Zc) extending through the catheter. The roll alignment feature allows the roll angle of the image reference frame of reference and coordinate system $(X_I, Y_I, Z_I)$ to be registered with respect to the catheter reference frame and coordinate system $(X_C, Y_C, Z_C)$. In some embodiments, the roll alignment feature is a shaped protrusion keyed to match a similarly shaped channel in the catheter. In alternative embodiments, the roll alignment feature may be a channel shaped to match a protrusion in the catheter. More than one roll alignment feature may be used to maintain the probe in a fixed orientation about the catheter roll axis. In another alternative embodiment, the roll angle of the image coordinate system with respect to the catheter coordinate system may be determined by a roll sensor located outside of the patient anatomy. In still another alternative embodiment, the roll angle may be determined by viewing one or more markers or other features with a known angle relative to the catheter in the image recorded by the imaging probe. For example, the feature or marker may be located on the circumference of the catheter and have a contrast (e.g. an ultrasound contrast) to the catheter. In another alternative embodiment, the combined roll and insertion length may be determined by observing a pattern on the probe around the proximal end of the catheter or by observing a pattern on the catheter around the proximal end of the probe. Various registration techniques (e.g., optical flow) may be used to register the image coordinate system and the catheter coordinate system.

Referring to FIG. 6, in some embodiments, the relative pose between the image coordinate system and the catheter coordinate system is determined using one or more external images, where each external image includes a catheter image and an image probe image. Such external images may be provided by computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like (e.g., fluoroscopy). In the example of FIG. 6, a display system 110 displays a concurrent or real-time external image 602 of the patient anatomy from an external fluoroscopy imaging device. The external image 602 includes images of the catheter 408, the ultrasound probe 406, and bones (e.g., ribs 604-1, 604-2) in the patent anatomy. In some embodiments, an operator may provide inputs (e.g., using an input device) to identify the locations of the ultrasound probe 406 and the distal end 410 of the catheter 408. In the example of FIG. 6, the display system 110 includes a touch screen, and the operator may use the touch screen to identify the distal end 410 of the catheter 408 (e.g., by using a marker "X") and the ultrasound probe 406 (e.g., by using a marker "A") in the external image 602. The operator may submit the identified locations to the control system by selecting a button 606.

In some embodiments, the control system may determine the relative pose between the image coordinate system and the catheter coordinate system by using an image analysis algorithm to analyze the image 602 to automatically detect the positions of the distal end 410 of the catheter 408 and the ultrasound probe 406 in the image 602. In some examples, known anatomical landmark dimensions in the image 602 (e.g., a distance d1 between successive ribs 604-1 and 604-2) may be used to determine the distance d2 between the positions of the distal end 410 of the catheter 408 and the ultrasound probe 406 in the image 602.

In some embodiments, two or more external images are used to determine the locations and/or the relative locations of the ultrasound probe 406 and the distal end 410 of the guided catheter 408. By using two or more external images, a three-dimensional image of the patient anatomy including the ultrasound probe 406 and the catheter 408 may be constructed from a plurality of two-dimensional external images based on the locations of the ultrasound probe 406 and the distal end 410 of the catheter 408 on each external image. The locations of the ultrasound probe 406 and the distal end 410 of the catheter 408 on each external image may be identified based on either operator inputs or digital imaging processing performed by the control system. In some embodiments, the two or more external images are provided by the same external imaging device (e.g., a fluoroscopy imaging device) from different view directions. In alternative embodiments, the two or more external images are provided two or more external imaging devices using different imaging technologies (computed tomography (CT), magnetic resonance imaging (MRI), fluoroscopy, thermography, ultrasound, optical coherence tomography (OCT), thermal imaging, impedance imaging, laser imaging, or nanotube X-ray imaging, etc.).

Referring to FIGS. 7, 8, and 9, in some embodiments, the catheter may provide an imaging probe (e.g., an ultrasound probe) concurrently with a tool. In those embodiments, the first image from the imaging probe may include both the tool and the target structure, which may be used to confirm or determine the positions of a tip of the tool and the target structure. In some embodiments, additional location data of the tip of the tool may be determined based on sources (e.g., external images of the patient anatomy, known pose of the distal end of the catheter) other than the first image, which may be used to determine the location of the target structure. By using the first image from the imaging probe and the location data of the tip of the tool, the position of the target structure may be determined during a medical procedure (e.g., biopsy, ablation, etc.). In an example, a virtual visualization image of the patient anatomy may be provided to an operator during a biopsy procedure, which includes an image of a biopsy instrument and an image of the target structure and provides visualization of the insertion of the biopsy instrument into a target structure.

Referring to the example of FIG. 7, illustrated is a virtual image 800 of a target structure 810 and nearby anatomic passageways 802. The passageways 802 include passageway walls 804. As shown in FIG. 7, a biopsy instrument 806 is inserted in a channel of the catheter 808 during a biopsy procedure. The catheter 808 may be steered to a position and/or orientation that provides access to the target structure 810. The steering of the catheter may be accomplished directly by active steering control of the catheter or indirectly by navigating a steerable biopsy instrument 806. The biopsy instrument 806 is extended from the catheter 808, through the wall 804 of the anatomic passageway 802 and into contact with the target structure 810 to allow a tissue sample to be taken, although in some examples, extension of biopsy instrument 806 may be delayed until the distal end 814 of the catheter 808 is properly positioned. In an alternative example, the biopsy instrument 806 may be replaced by a treatment device such as an ablation tool or dissection tool.

In the example of FIG. 7, the catheter 808 includes an integrated imaging probe 812 (e.g., an ultrasound probe) at a distal end 814 of the catheter 808. In alternative embodiments, an imaging probe (e.g., an ultrasound probe) may simultaneously be inserted through a second channel of the catheter, while the biopsy instrument is inserted through a first channel of the catheter. The imaging probe 812 is located in passageways 802 to take intra-operative and real-time images of the biopsy instrument 806 and the target structure 810. In various embodiments, those images of the biopsy instrument 806 and the target structure 810 may be used to further aid in registering the images captured by the imaging probe 812 and/or localizing imaging probe 812 relative to the target structure 810, biopsy instrument 806 and the tool tip 816 of the biopsy instrument 806.

In the example of FIG. 7, the imaging probe 812 is a forward-facing ultrasound probe, which is used to capture images of both target structure 810 and biopsy instrument 806 (e.g., as the biopsy instrument 806 penetrates the target structure 810) that are distal of the imaging probe 812. In alternative embodiments, the imaging probe 812 includes a side-imaging probe for capturing images of both target structure 810 and biopsy instrument 806 by generating a cross-sectional (i.e., radial) image along an imaging plane of the side-imaging probe 812 (e.g., the imaging plane 412 of the imaging probe 406 of FIG. 4). In various embodiments, by using an ultrasound probe, images of objects located outside of the anatomic passageways (e.g., the target structure 810, a portion of the biopsy instrument 806) may be captured.

Referring to the example of FIG. 8, illustrated is an image 850 generated by a forward-facing ultrasound probe 812 shown in FIG. 7. The image 850 has an image frame of reference and coordinate system $(X_I, Y_I, Z_I)$, and includes an image of the target structure 810 and an image of the biopsy instrument 806 including its tool tip 816. In various embodiments, the target structure 810, biopsy instrument 806, and tool tip 816 are identified in the image frame of reference. They may be identified, for example, by an operator (e.g., a clinician), by an image analysis algorithm, or by a combination of the two. Although the image 850 is two-dimensional, a three-dimensional image may be constructed from a plurality of two-dimensional ultrasound images. Data associated with the locations of the target structure 810 and the tool tip 816 in the image frame of reference is transformed to the catheter coordinate system or the patient coordinate system (that has been registered with the catheter coordinate system). The location data of the target structure 810 and the tool tip 816 in the catheter coordinate system or the patient coordinate system may be used to provide a visual virtualization image on the display system 110.

In various embodiments, in addition to first location data of the tool tip 816 determined based on the image 850 provided by the imaging probe 812, second location data of the tool tip 816 based on sources (e.g., a known pose of the distal end 814 of the catheter 808, an external image from an external imaging device) may be used to determine the location of the target structure 810. In some embodiments, such second location data of the tool tip 816 is determined based on a known pose of the distal end 814 of the catheter 808. For example, the second location data of the tool tip 816 may indicate that the tool tip 816 is along the same direction as the distal end 814 of the catheter 808. For further example, the second location data of the tool tip 816 may indicate that the tool tip 816 is at a predetermined distance (e.g., 15 mm) from the distal end 814 of the catheter 808.

Referring to FIG. 9, in some embodiments, second location data of the tool tip 816 may be determined based on an external image of the patient anatomy provided by an external imaging device. FIG. 9 illustrates a display system 110 displaying a concurrent or real-time external image 902 of the patient anatomy from an external fluoroscopy imaging device. The external image 902 includes images of a catheter 808, an ultrasound probe 812 integrated at a distal end 814 of the catheter 808, a biopsy instrument 806, and a tool tip 816 of the biopsy instrument 806.

In some embodiments, an operator (e.g., a clinician) may provide inputs (e.g., using an input device) to identify the locations of the distal end 814 of the catheter 808 and the tool tip 816 in the external image 902. In the example of FIG. 9, the display system 110 includes a touch screen, and the operator may use the touch screen to identify the location of the distal end 814 of the catheter 808 (e.g., using a marker "X"), and to identify the location of the tool tip 816 (e.g., using a marker "A") on the external image 902. The operator may then submit the identified locations to the control system (e.g., using a button 906).

In some embodiments, the control system may identify the locations of the distal end 814 of the catheter 808 and the tool tip 816 in the external image 902 by using an image analysis algorithm. For example, the image analysis algorithm may be used to automatically detect the distal end 814 of the catheter 808 and the tool tip 816 in the external image 902. In some examples, known anatomical landmark dimensions in the external image 902 (e.g., a distance d3 between successive ribs 904-1 and 904-2) may be used to determine the distance d4 between the distal end 814 of the catheter 808 and the tool tip 816.

Referring to the example of FIG. 10, illustrated is a method 1000 for determining the target structure location using the imaging probe according to some embodiments. The method 1000 is illustrated as a set of operations or processes 1002 through 1014. Not all of the illustrated processes 1002 through 1014 may be performed in all embodiments of method 1000. Additionally, one or more processes that are not expressly illustrated in FIG. 10 may be included before, after, in between, or as part of the processes 1002 through 1014. In some embodiments, one or more of the processes may be implemented, at least in part, in the form of executable code stored on non-transitory, tangible, machine-readable media that when run by one or more processors (e.g., the processors of control system 112) may cause the one or more processors to perform one or more of the processes.

The method 1000 begins at a process 1002, where a first image of an anatomic structure is received from an imaging probe (e.g., an ultrasound probe) located inside a patient anatomy. In some embodiments, as shown in FIG. 4, the imaging probe 406 is extendable distally beyond a distal end 410 of a catheter 408. At the process 1002, a control system 112 receives an image 500 of FIG. 5 of an anatomic structure including a target structure $P_f$ from the imaging probe 406 of FIG. 4. In alternative embodiments, as shown in FIG. 7, the imaging probe 812 is integrated with a catheter 808 and located at a distal end 812 of the catheter 808. At the process 1002, a control system 112 receives an image 850 of FIG. 8 of an anatomic structure including a target structure 810 captured by the imaging probe 806 of FIG. 7. In yet other alternative embodiments, an imaging probe may simultaneously be inserted through a second channel of the catheter, while an instrument (e.g., a biopsy instrument) is inserted through a first channel of the catheter.

At a process 1004, the control system 112 receives one or more external images of the patient anatomy from an external imaging device located outside the patient anatomy, where such external images include images of the catheter, the imaging probe, and/or the instrument. In some embodiments, as shown in FIG. 6, a control system 112 receives one or more external images 602 of FIG. 6 from an external imaging device located outside the patient anatomy. Each of the external images includes an image of the catheter 408 and an image of the imaging probe 406 of FIG. 4. In some embodiments, as shown in FIG. 9, a control system 112 receives one or more external images 902 of FIG. 9 from an external imaging device located outside the patient anatomy. Each of the external images 902 includes an image of the catheter 808, and an image of the imaging probe 812, and a tool 806 of FIG. 8.

The method 1000 may then proceed to a process 1010, where a relative pose between an image reference frame associated with the imaging probe and a catheter reference frame associated with the distal end of the catheter is determined. Such a relative pose may be used to transform location data of the target structure and instrument (e.g., a tool tip) in the first image of the image reference frame to the catheter reference frame. In some embodiments, the relative pose may be measured directly by sensors on the catheter and imaging probe. Such sensors may include an EM sensor, a fiber optic shape sensor, or the like. In alternative embodiments, the relative pose may be determined based by using two or more external images (e.g., provided by an external imaging device with different view directions to the patient anatomy). In those embodiments, three-dimensional positions of both the imaging probe and the catheter may be determined using the two or more external images, and the relative pose may be determined using those three-dimensional positions of the imaging probe and the catheter.

In some embodiments, the process 1010 uses a process 1006 for determining a relative position between the imaging probe and the distal end of the catheter based on one or more external images, and uses a process 1008 for determining a relative orientation between the imaging probe and the distal end of the catheter. In those embodiments, the process 1010 determines the relative pose using the relative position determined at the process 1006 and the relative orientation determined at the process 1008.

In some embodiments, at the process 1006, a relative position between the imaging probe and the distal end of the catheter is provided by assuming a constant distance (e.g., 15 mm) between the imaging probe and the distal end of the catheter and by assuming that the imaging probe is along the same direction as the distal end of the catheter. In another alternative embodiment, as shown in FIGS. 6 and 9, the relative position between the imaging probe and the distal end of the catheter is determined based on one or more external images (e.g., using operator inputs, image analysis algorithm, and/or a combination thereof). For example, as shown in FIG. 6, the positions of the distal end 410 of the catheter 408 and the imaging probe 406 in the external images 602 may be identified by operator inputs, an image analysis algorithm, and/or a combination thereof.

At the process 1008, a relative orientation between the imaging probe and the distal end of the catheter is determined. In some embodiments, at the process 1008, the catheter is navigated to a catheter park location, where a distal end of the catheter is aligned with an anatomical landmark (e.g., a bifurcation). In those embodiments, a relative orientation between the imaging probe and the distal end of the catheter is determined based on the same anatomical landmark detected in the first image from the imaging probe (e.g., using operator inputs, image analysis algorithm, and/or a combination thereof). In alternative embodiments, the imaging probe is directly integrated in the catheter to maintain a fixed orientation. In an example, the imaging probe may be embedded at the distal end of the catheter. In another example, the imaging probe may include a roll alignment feature keyed to the catheter to cause the imaging probe to maintain a fixed orientation about a catheter roll axis (Zc) extending through the catheter. In yet another example, the imaging probe is surrounded by at least in part by a sheath rotatably fixed (e.g., keyed) relative to the catheter. The keyed sheath may include one or more markers (e.g., echogenic features) for generating an identifiable region in the first image, which may then be used as a reference roll angle between the imaging probe and the distal end of the catheter. In yet other alternative embodiments, a roll angle between the imaging probe and the catheter may be determined using a roll sensor located outside of the patient anatomy. In another embodiment, the catheter is directed such that the target is in about the middle of the image. In that embodiment, the catheter is directed such that the target is straight ahead along the catheter shaft, and the relative orientation between the imaging probe and the distal end of the catheter may not be needed.

At a process 1012, for a catheter that provides an imaging probe and a tool simultaneously (e.g., during biopsy), first location data and second location data for a tip of the tool are determined. As shown in FIG. 8, first location data for the tool tip is determined using the image 850 provided by the imaging probe 812 of FIG. 7. As shown in FIG. 9, second location data for the tool tip is determined based on the external image 902 provided by an external imaging device (e.g., using operator inputs, image analysis algorithm, and/or a combination thereof).

At a process 1014, location data of the target structure in catheter reference frame and/or the patient reference frame may be determined based on location data of the target structure in the image reference frame, the relative pose between the imaging probe and the distal end of the catheter, first tool tip location data, second tool tip location data, and/or a combination thereof. For example, location data of a target structure in the first image may be transformed from the image reference frame to the catheter reference frame based on the relative pose. For further example, the location data of the target structure in the catheter reference frame may be transformed to a patient reference frame. Those location data of the target structure in the catheter reference frame and/or patient reference frame may be used to provide a virtual visualization image of the patient anatomy including the target structure to an operator.

Figure 12A:
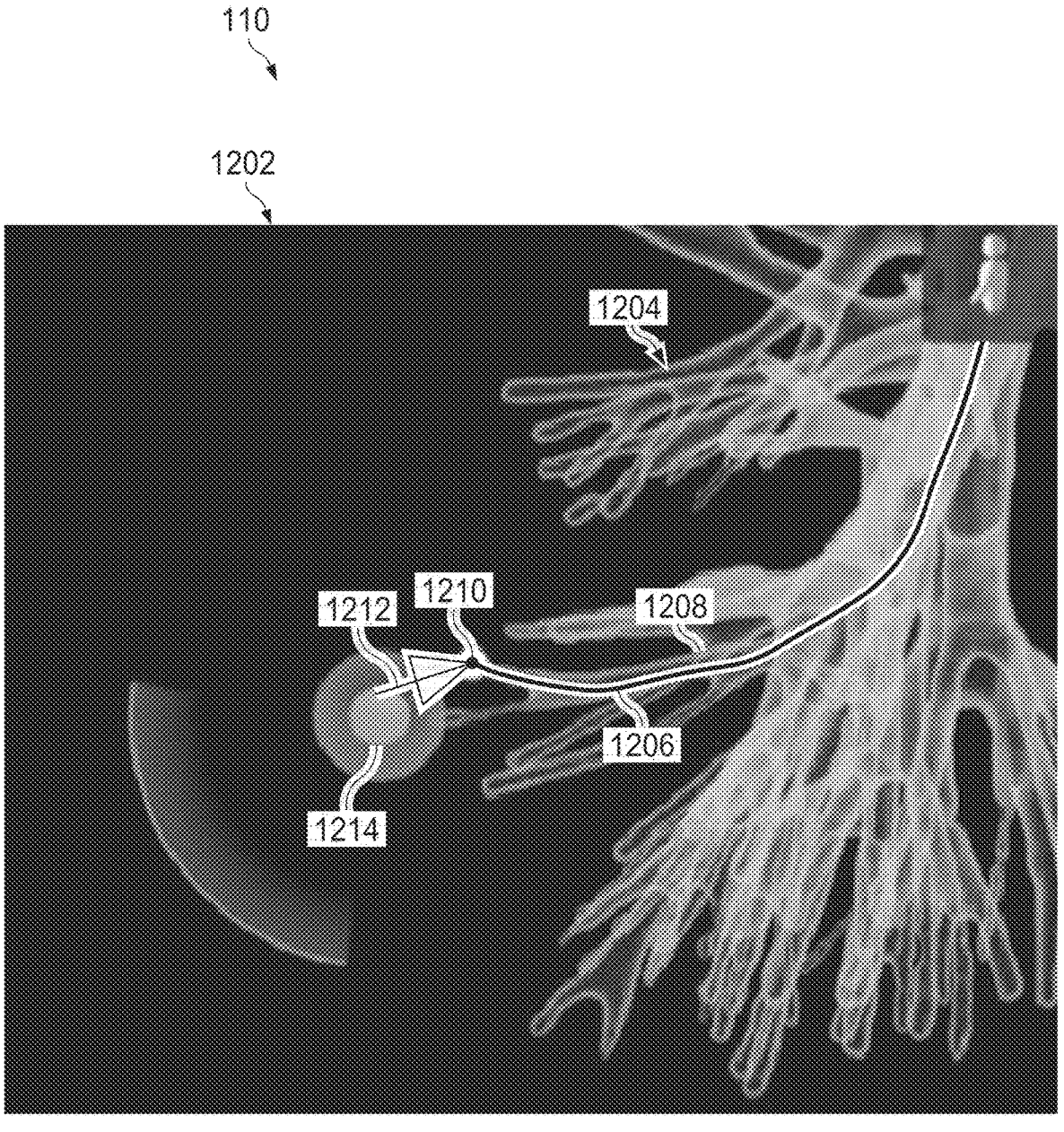
FIG. 12A illustrates a virtual visualization image according to some embodiments.
Figure 12B:
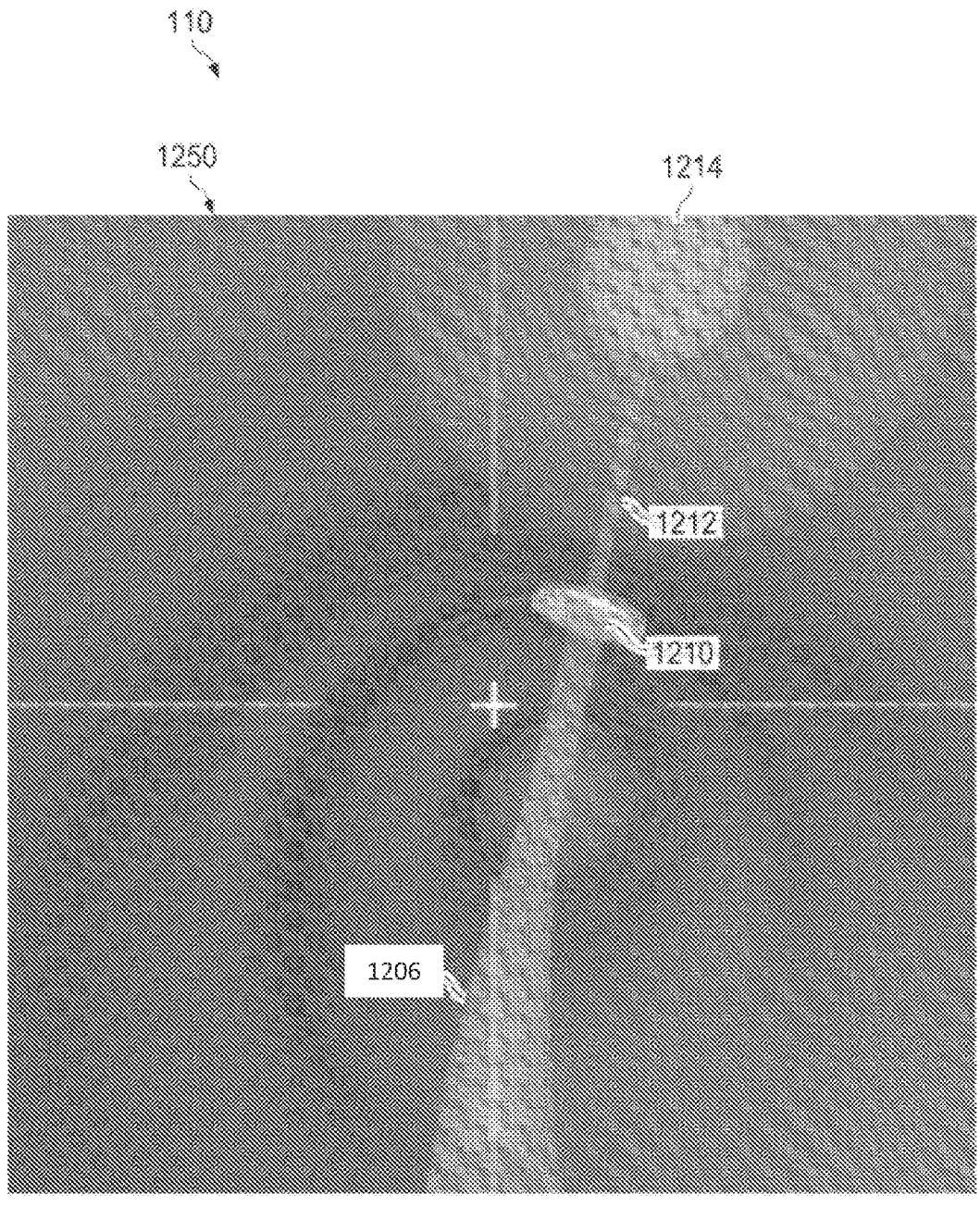
FIG. 12B illustrates a virtual visualization image according to some embodiments.
Figure 13:
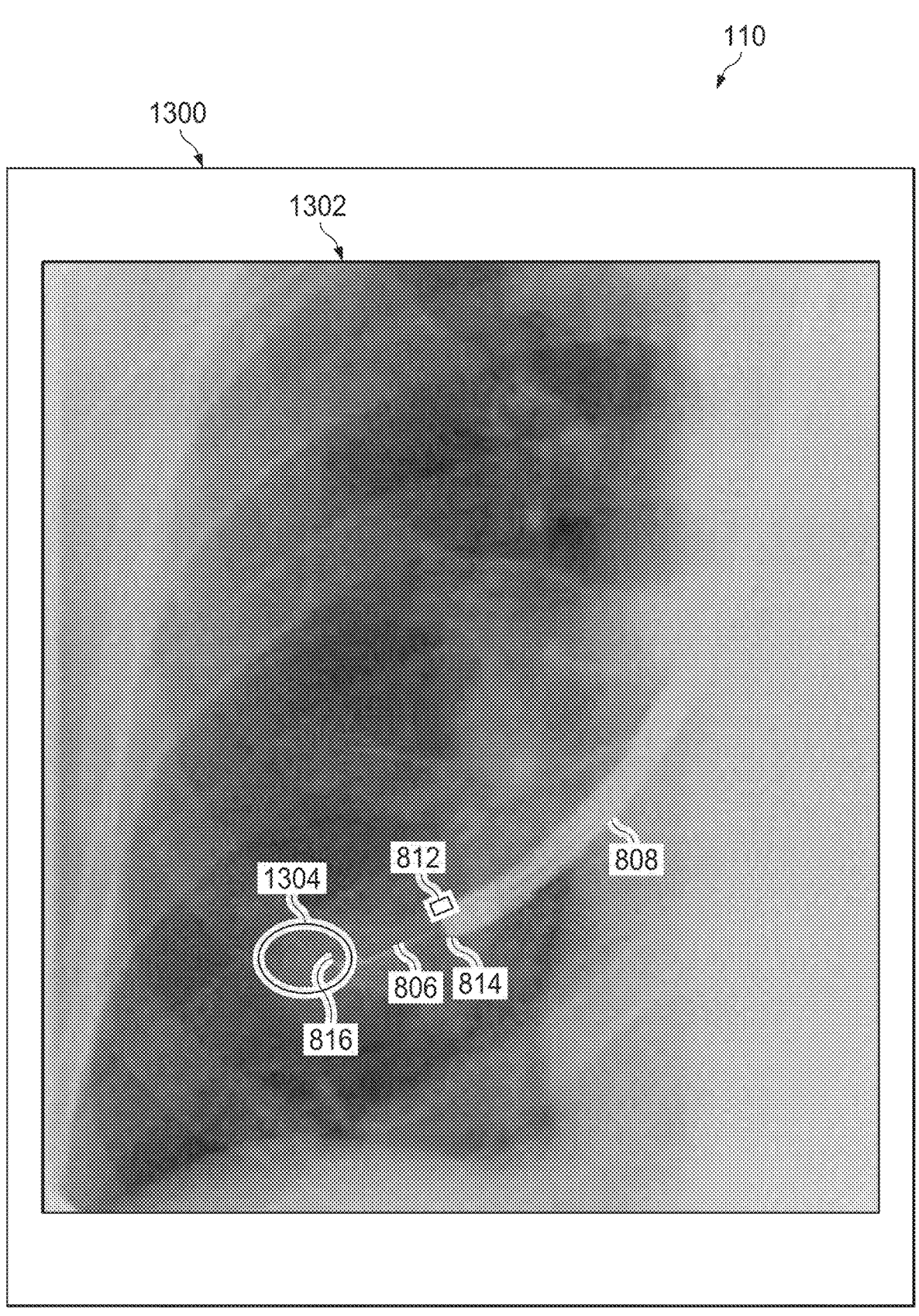
FIG. 13 illustrates a virtual visualization image according to some embodiments.
Figure 14:
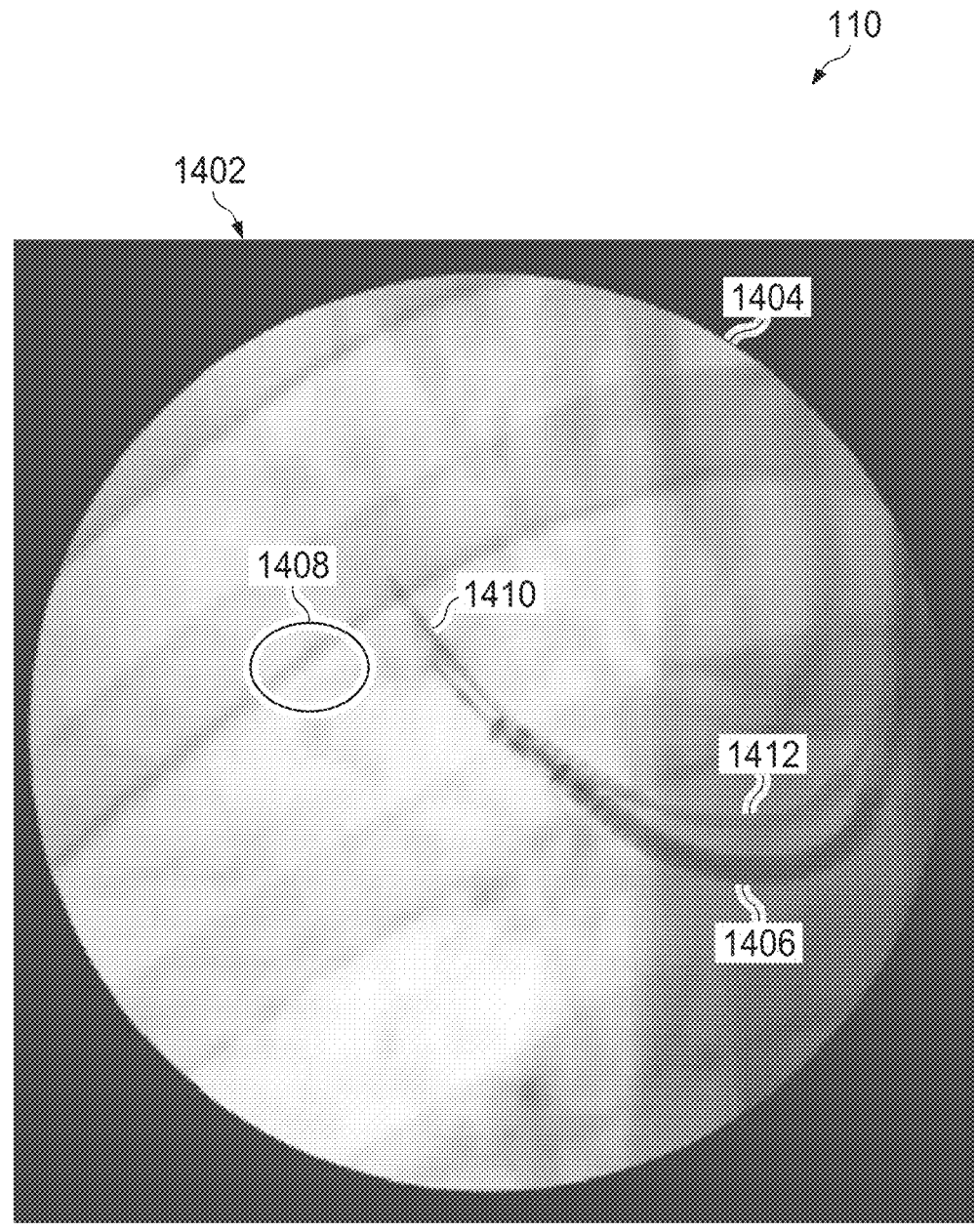
FIG. 14 illustrates a virtual visualization image according to some embodiments.

Referring to FIGS. 11, 12A, 12B, 13, and 14, various visual virtualization images may be provided to an operator using the location data of the target structure in the catheter reference frame and/or patient reference frame. FIG. 11 illustrates a method 1100 for presenting the target structure in virtual visualization images on a display system using the location data of the target structure determined based on a first image from the imaging probe. FIGS. 12A-12B illustrate various virtual visualization images including virtual representation of the target structure in an anatomic model of the patient anatomy. FIGS. 13 and 14 illustrate various virtual visualization images including virtual representation of the target structure in an external image of the patient anatomy.

Referring to FIG. 11, illustrated is a method 1100 for presenting the target structure in virtual visualization images on a display system using the location data of the target structure determined based on a first image from the imaging probe. The method 1100 is illustrated as a set of operations or processes 1102 through 1110. Not all of the illustrated processes 1102 through 1110 may be performed in all embodiments of method 1100. Additionally, one or more processes that are not expressly illustrated in FIG. 11 may be included before, after, in between, or as part of the processes 1102 through 1110. In some embodiments, one or more of the processes may be implemented, at least in part, in the form of executable code stored on non-transitory, tangible, machine-readable media that when run by one or more processors (e.g., the processors of control system 112) may cause the one or more processors to perform one or more of the processes.

The method 1100 begins at a process 1102, where location data of a target structure transformed to a visualization reference frame (e.g., a model reference frame associated with an anatomic model or a patient reference frame associated with an external image) is received. The location data of the target structure in the visualization reference frame may be determined based on an image provided by an imaging probe as described in the method 1000.

At a process 1104, in some embodiments, a virtual visualization image including an image of an anatomic model of the patient anatomy and an image of the target structure, is provided to an operator. In those embodiments, the visualization reference frame is the model reference frame. Referring to FIG. 12A, in some examples, the virtual visualization image includes a global view of the anatomic model. Specifically, as illustrated in FIG. 12A, in some examples, the display system 110 displays a virtual visualization image 1202 of the patient anatomy as an anatomic model 1204 including passageways. The anatomical model 1204 can be generated from pre-operative or intra-operative gathered using an external imaging source as previously described. The virtual visualization image 1202 can additionally provide a visual representation of a concurrent, updated, or real-time image of the target structure 1214 using location data of the target structure 1214 in the model reference frame. In some embodiments, the image of the target structure 1214 is a three-dimensional image generated using a plurality of images provided by the imaging probe. By projecting an image of the target structure 1214 with a correct location and orientation in the virtual visualization image 1202 based on one or more images provided by the imaging probe, the virtual visualization image 1202 provides an operator improved spatial awareness of the location of the target structure where the lesion was located. Additionally, the virtual visualization image 1202 can include concurrent or real time virtual images of a catheter 1206 in a passageway 1208 of the anatomic model 1204, and a tool 1212 extending from a distal end 1210 of the catheter 1206.

As illustrated in FIG. 12B, in some examples, the display system 110 displays a concurrent or real-time virtual visualization image 1250 of the patient anatomy that includes an internal view of a passageway 1208 of the anatomic model 1204 of FIG. 12A. The virtual visualization image 1250 provides a virtual image of a catheter 1206 and a tool 1212 extending from a distal end 1210 of the catheter 1206.

At a process 1106, in some embodiments, a virtual visualization image includes an image on an anatomic model of the patient anatomy including an updated target location of the target structure determined based on images provided by the imaging probe. Such an updated target location may further provide a better aiming direction for optimal access to the target structure.

In some embodiments, at process 1106, the virtual visualization image includes an indication of an optimal catheter park location for optimal access to the target structure based on images provided by the imaging probe. In some embodiments, the optimal catheter park location is determined based on a plurality of sequential images captured by the imaging probe when the imaging probe is at a plurality of different locations of the passageway 1208 (e.g., at different locations of a segment of the passageway 1208 that allow capturing images of the target structure) and/or at different orientations. For each of those sequential images, a target structure surface area measurement is computed (e.g., using a ratio of a target structure pixel number over a total number of pixels of the image). In some embodiments, the target structure surface area measurements may guide the imaging probe to an optimal pose that maximizes the target structure surface measurement. In some embodiments, an optimal catheter park location and/or optimal catheter orientation (e.g., for performing biopsy) are determined based on the optimal imaging probe pose.

In some embodiments, automated optimization may be used to generate a catheter driving path determined based the target structure surface area measurements. The catheter driving path may allow the catheter to drive along the gradients of the target structure surface area measurements to achieve the optimal target structure surface measurement. In some examples, the optimal catheter park location and optimal catheter orientation may be used to drive automatic scanning with the tip of the catheter in an area.

At a process 1108, a virtual visualization image including an external image from an external imaging device outside of a patient anatomy and an image of the target structure is provided to an operator. An image of the target structure is provided in the virtual visualization image using location data of the target structure in the patient reference frame. For example, as shown in FIG. 13, a display system 110 includes a virtual visualization image 1300, which includes a real-time external image 1302 during biopsy. The real-time external image 1302 includes images of the catheter 808, an imaging probe 812 integrated to a distal end 814 of the catheter 808, a tool 806, and a tool tip 816. An image of the target structure 1304 is provided in the virtual visualization image using location data of the target structure provided by the imaging probe in the patient reference frame. In the example of FIG. 13, a virtual visualization of an insertion of the tool tip 816 into the target structure 1304 during biopsy is realized by using an imaging probe that captures images of both the target structure 1304 and the tool tip 816.

At a process 1110, a virtual visualization image including an external image from an external imaging device outside of a patient anatomy and a reference catheter image based on location data of the imaging probe is provided to an operator. In the example of FIG. 14, a display system 110 includes a virtual visualization image 1402. The virtual visualization image 1402 includes a real-time external image 1404 during biopsy, which includes a real-time image for the catheter 1406. At the process 1110, an imaging probe is removed from a channel of the catheter, and a tool 1410 (e.g., a biopsy needle) is inserted into that channel. In the example of FIG. 14, an image of a target structure 1408 is provided in the external image 1404 based on location data of the target structure in the patient reference frame. Furthermore, a reference image of a catheter 1412 is provided in the external image 1404 based on previously collected location data of the imaging probe and the catheter when the imaging probe is driven to capture the image of the target structure.

The systems and methods of this disclosure may be used for connected bronchial passageways of the lungs. The systems and methods may also be suited for navigation and treatment of other tissues, via natural or surgically created connected passageways, in any of a variety of anatomic systems including the colon, the intestines, the kidneys, the brain, the heart, the circulatory system, or the like. The systems and methods may also be suitable for navigation around the traceable surface of an organ. The methods and embodiments of this disclosure are also suitable for non-surgical applications.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
a catheter including a first channel and a distal end, wherein the distal end is associated with a catheter frame of reference; and
a processor configured to:
  receive a first image captured by a first imaging device movable within and extendable from the catheter within a patient anatomy;
  receive a second image of the patient anatomy captured by a second imaging device from outside the patient anatomy, wherein the second image includes the catheter and the first imaging device, wherein the second image is received while the first imaging device is extended from the distal end of the catheter;
  determine, while the first imaging device is extended from the distal end of the catheter, a relative pose between the first imaging device and the distal end of the catheter based on the second image by identifying, in the second image, a location of the first imaging device and a location of the distal end of the catheter by:
    performing image analysis of the second image; or
    receiving a user input identifying the location of the first imaging device in the second image and receiving a user input identifying the location of the distal end of the catheter in the second image;
  determine a target location associated with a target structure in the first image; and
  transform the target location in an image frame of reference associated with the first image to the catheter frame of reference based on the relative pose.

2. The medical system of claim 1, wherein the first imaging device includes an ultrasound probe.

3. The medical system of claim 2, wherein the ultrasound probe is configured to be slidably received within the first channel of the catheter; and wherein a tool is configured to be slidably received within a second channel of the catheter.

4. The medical system of claim 3, wherein the processor is configured to:
  determine a tool tip location of a tool tip of the tool in the first image; and
  transform the tool tip location from the image frame of reference to the catheter frame of reference.

5. The medical system of claim 1, wherein the first imaging device is extendable distally beyond the distal end of the catheter, and wherein to determine the relative pose, the processor is configured to:
  determine a first distance between the distal end of the catheter and the first imaging device using the second image.

6. The medical system of claim 5, wherein the first distance between the distal end of the catheter and the first imaging device is measured automatically by performing the image analysis of the second image.

7. The medical system of claim 6, wherein to determine the relative pose, the processor is configured to:
  receive a third image of the patient anatomy captured by a third imaging device from outside the patient anatomy, wherein the third image includes the catheter and the first imaging device; and
  determine a relative position between the first imaging device and the distal end of the catheter based on the second image and third image.

8. The medical system of claim 5, wherein the first distance is determined based on an anatomical landmark dimension in the second image.

9. The medical system of claim 1, further comprising a display, wherein the processor is further configured to:
  transform the target location in the catheter frame of reference to a patient model frame of reference of a patient model; and
  display, on the display, a virtual visualization image including an image of the patient model with an image of the target structure based on the target location in the patient model frame of reference.

10. The medical system of claim 1, wherein the patient anatomy is within a patient body, and wherein the second imaging device is positioned outside the patient body.

11. A method performed by a computing system, the method comprising:
  receiving a first image of an anatomic structure from an imaging probe inside a patient anatomy, the first image having an image frame of reference, wherein the imaging probe is movable within and extendable distally beyond a distal end of a catheter, the distal end of the catheter having a catheter frame of reference;
  receiving a first external image of the patient anatomy from a first external imaging device, wherein the first external image includes the catheter and the imaging probe, wherein the first external image is received while the imaging probe is extended from the distal end of the catheter;
  determining, while the imaging probe is extended from the distal end of the catheter, a relative pose between the imaging probe and the distal end of the catheter based on the first external image by identifying, in the first external image, a location of the imaging probe and a location of the distal end of the catheter by:
    performing image analysis of the first external image; or
    receiving a user input identifying the location of the imaging probe in the first external image and receiving a user input identifying the location of the distal end of the catheter in the first external image;
  determining a target location associated with a target structure in the first image; and
  transforming the target location in the image frame of reference to the catheter frame of reference based on the relative pose.

12. The method of claim 11, wherein the determining of the relative pose between the imaging probe and the distal end of the catheter comprises:
  using the first external image to determine a first distance between the distal end of the catheter and the imaging probe.

13. The method of claim 12, wherein the performing image analysis of the first external image includes:
  determining the first distance between the imaging probe and the distal end of the catheter based on an anatomical landmark dimension in the first external image.

14. The method of claim 12, further comprising:
  receiving a second external image of the patient anatomy from the first external imaging device, wherein the second external image includes the catheter and the imaging probe; and determining the first distance based on the first external image and the second external image, wherein the first external image is associated with a first view direction of the first external imaging device, and wherein the second external image is associated with a second view direction of the first external imaging device different from the first view direction.

15. The method of claim 11, further comprising:

transforming the target location in the catheter frame of reference to a patient model frame of reference of a patient model; and displaying, on a display of a navigation system, a virtual visualization image including an image of the patient model with an image of the target structure based on the target location in the patient model frame of reference.

16. The method of claim 11, further comprising:

transforming the target location in the catheter frame of reference to a patient frame of reference associated with a patient; and displaying, on a display of a navigation system, a virtual visualization image including a second external image of the patient anatomy with an image of the target structure based on the target location in the patient frame of reference.

17. The method of claim 11, further comprising:

receiving a first plurality of images of the anatomic structure from the imaging probe at a plurality of imaging probe poses;

analyzing the first plurality of images to determine corresponding surface area measurements of the target structure in the first plurality of images; and determining a first imaging probe pose for maximizing the surface area measurement based on the surface area measurements of the target structure in the first plurality of images.

18. The method of claim 17, further comprising:

generating a path based on the surface area measurements of the target structure.

19. The method of claim 17, further comprising:

determining a first catheter pose for maximizing the surface area measurement based on the surface area measurements of the target structure in the first plurality of images.

* * * * *